United States Patent [19]

Blumberg et al.

[11] 4,189,464
[45] Feb. 19, 1980

[54] HEPATITIS B TESTING REAGENT AND METHOD

[75] Inventors: Baruch S. Blumberg, Philadelphia; Irving Millman, Willow Grove, both of Pa.

[73] Assignee: Institute for Cancer Research, Philadelphia, Pa.

[21] Appl. No.: 903,238

[22] Filed: May 5, 1978

[51] Int. Cl.$^2$ .................... G01N 33/16; A61K 43/00; G21H 5/02

[52] U.S. Cl. .................... 424/1; 23/230 B; 424/12

[58] Field of Search .................... 424/1, 1.5, 81, 12; 23/230 B

[56] References Cited

U.S. PATENT DOCUMENTS

| | | | |
|---|---|---|---|
| 3,646,346 | 2/1972 | Catt | 23/230 B |
| 3,867,517 | 2/1975 | Ling | 424/1 |
| 3,872,225 | 3/1975 | Coller | 424/1 |
| 3,904,367 | 9/1975 | Goubersuch | 23/230 B |
| 4,012,494 | 3/1977 | Ling | 424/1 |
| 4,041,146 | 8/1977 | Giaever | 424/1 |
| 4,067,959 | 1/1978 | Bolz | 424/1 |
| 4,092,408 | 5/1978 | Litt | 424/1 |
| 4,108,972 | 8/1978 | Dreyer | 424/1 |

FOREIGN PATENT DOCUMENTS

1486826  9/1977  United Kingdom .................... 424/1

OTHER PUBLICATIONS

Salmon et al, J. of Immunology, vol. 103, 1969, pp. 129-137.
Salmon et al, J. of Immunology, vol. 104, 1970, pp. 665-672.

*Primary Examiner*—Benjamin R. Padgett
*Assistant Examiner*—Christine M. Nucker
*Attorney, Agent, or Firm*—Dann, Dorfman, Herrell & Skillman

[57] ABSTRACT

A test reagent reagent for $HB_sA_g$ is prepared by applying to a suitable substrate, such as a polystyrene bead, a first coat of purified $HB_sA_g$ to an extent which will permit complete coverage by anti-$HB_s$. After washing $HB_sA_g$ coated substrate, serum containing anti-$HB_s$, or an IgG fraction of serum containing anti-$HB_s$, is applied as a second coat as a second coat in an amount which substantially completely occupies the reacting sites of the $HB_sA_g$ on the outside of the substrate and leaves an excess of antibody reacting groups in a free state, and any unattached material is washed off.

A test sample which is to be tested for $HB_sA_g$ is then contacted with the reagent thus produced, permitting attachment of $HB_sA_g$ if present, and washing is done.

Then a source of anti-$HB_s$, such as an IgG fraction containing anti-$HB_s$, which has been radioactively labeled, is brought into contact with the reagent is brought into contact with the reagent, and any unattached material is washed off. The presence or absence of $HB_sA_g$ in the test sample is determined sample is determined from the presence or absence of significant additional radiation coming from the reagent as compared with a control.

This method and its double coated test reagent permits securing high sensitivity without any manufacture of "dissociated" anti-$HB_s$ separately from the process itself, for use at any stage of the process, which separate manufacture of "dissociated" anti-$HB_s$ is a difficult and expensive procedure which adds greatly to the expense of any radioimmunoassay which calls for it to be done.

23 Claims, 4 Drawing Figures

HEPATITIS B TESTING REAGENT AND METHOD

GENERAL DESCRIPTION, INCLUDING SOME BACKGROUND MATERIAL

The present invention relates to a radioimmunoassay involving Australia antigen. The latter has been renamed over the past years; such names as hepatitis associated antigen (HAA), serum hepatitis antigen (SH), hepatitis B antigen and hepatitis B surface antigen ($HB_sA_g$) are recognized as the same by experts in the field. Throughout this disclosure, Australia antigen will be referred to as $HB_sA_g$, which is generally accepted worldwide.

The present assays for $HB_sA_g$ which are most widely used because of their sensitivity and accuracy are the radio-immunoassays. The current ones available make use of a substrate, usually a plastic bead, on to which is very likely to be attached an IgG (immunoglobulin) fraction of anti-$HB_s$ antiserum. The latter is either from a human donor or from immunized animals such as rabbits, guinea pigs, horses, sheep, goats, etc. This IgG fraction is composed of several antibodies which include the antibody to $HB_sA_g$ (anti-$HB_s$). Other antibodies which may be expected in such antisera are antibodies to other agents to which the animal was exposed. For example, humans may be expected to have antibodies to every agent to which they were ever exposed. These may include polio, measles, pertussis, diphtheria and tetanus toxoids, for example. Therefore the IgG fraction of any antiserum should be expected to contain a variable amount of specific antibody to $HB_sA_g$, and that amount being probably no more than 1% of the total globulin fraction. Thus, with some prior art assay reagents, the $HB_sA_g$ in a test sample will combine with the small amount of anti-$HB_s$ on the plastic bead. A radioactively labeled anti-$HB_s$ (labeled with iodine 125) is next added to combine with the $HB_sA_g$ forming a sandwich of anti-$HB_s$- $HB_sA_g$-labeled anti-$HB_s$. This bead is then placed in a gamma counter to measure the amount of radioactivity. The greater the amount of radioactivity relevant to controls (normal human sera), the greater the amount of $HB_sA_g$. Assays such as the one described above have been described in publications (Purcell, R. H., Gerin, J. L., Almeida, J. B., and Holland, P. V., Intervirology 2: 231-243 (1973/74) and Purcell, R. H., Wong, D. C., Alter, H. J., and Holland, P. V., Appl. Microbiol. 26:478-484 (1973).

However, in order to have any reasonable chance of getting any really good sensitivity in a test along the above lines, "dissociated" anti-$HB_s$ must be made and used either as the radioactive labeled anti-$HB_s$, or for use instead of the IgG fraction to initially coat the solid substrate involved.

Unfortunately, the making of "dissociated" antibody for such a purpose is quite difficult and expensive, so that its making and use adds greatly to the total expense involved in any radioimmunoassay for hepatitis B which uses it thus.

"Dissociated" antibody is made by reacting purified $HB_sA_g$ with the IgG fraction containing anti-$HB_s$, washing the complex, and then dissociating or separating the anti-$HB_s$ from the $HB_sA_g$. There are several ways of accomplishing this and the one preferred today is known as affinity chromatography. Purified $HB_sA_g$ is attached to some solid material such as Sepharose B (Pharmacia) resin which is poured into a column. The IgG fraction containing anti-$HB_s$ is allowed to filter through. Anti-$HB_s$ reacts and combines with $HB_sA_g$. The column is washed and sodium thiosulfate or some other known reagent for dissociation of antigen-antibody complexes is added. The anti-$HB_s$ fraction is recovered, dialyzed and concentrated and can then be used.

"Dissociated" antibody is difficult to produce with any consistency and the process is expensive. Problems usually arise because of low yields (due to incomplete dissociation) and yields of anti-$HB_s$ with low combining power (avidity). The reason for the latter in unknown but may be due to incomplete uncovering of all anti-$HB_s$ combining sites or denaturation or both.

The present invention provides a better reagent which is sensitive and at the same time relatively inexpensive to produce.

The present invention secures high sensitivity without the great added expense of making up "dissociated" anti-$HB_s$ separately. It does this by making a solid phase reagent in which the substrate has two coats or layers, the first of which is purified $HB_sA_g$ and the second of which is anti-$HB_s$ which has been contacted with the $HB_sA_g$ in no very purified form. In other words the second coat is not a separately made "dissociated" form of anti-$HB_s$, but an ordinary source which contains anti-$HB_s$ as part of a very impure material, such as (especially) antiserum containing anti-$HB_s$ or an IgG fraction of antiserum containing anti-$HB_s$.

The first coat, the purified $HB_sA_g$, is applied on the substrate to an extent which permits its complete coverage by anti-$HB_s$. The second coat, which comprises anti-$HB_s$, must be applied in an quantity which completely covers the $HB_sA_g$, occupying substantially completely the reacting sites of the $HB_sA_g$, and includes an excess of antibody reacting sites which remain free.

The $HB_sA_g$ coat is allowed to select, by specific reaction, the antibody, anti-$HB_s$. Therefore, a second coat or layer results which is exclusively specific antibody to $HB_sA_g$. Since the second coat, like other antibodies used in such assays, has molecules each with two reactive sites, and a suitable excess of the anti-$HB_s$ has been applied, some of the antibody binding sites are available for further reaction, so that, the anti-$HB_s$ can combine with $HB_sA_g$ in test samples. In effect the reagent of the invention is highly specific because the antibody comprising the second coat is specific antibody capable of reacting with $HB_sA_g$ and only $HB_sA_g$.

A purpose of the present invention is to provide a highly sensitive solid state $HB_sA_g$ assay whose expense will be greatly reduced.

Describing the present invention somewhat more specifically, a polystyrene bead or other appropriate substrate is first coated with purified $HB_sA_g$. The extent of purification required will be discussed further hereinbelow. In making this coating, care should be taken that it be done only to an extent which is capable later of being entirely covered with anti-$HB_s$.

Then after washing, the antigen-coated bead is allowed to react with a source of anti-$HB_s$, to completely cover the $HB_sA_g$ with the anti-$HB_s$, and also to provide on the bead an excess of antibody reacting groups which remain free.

After washing, there is thus secured a reagent in the form of a doubly coated bead or other substrate whose under-coating layer is $HB_sA_g$ limited in extent to that which can be completely covered with anti-$HB_s$, and whose outermost layer is a complete covering made up of anti-HB$_s$ and that alone, and in an amount which includes an excess of antibody reacting groups which remain free.

Once this reagent is made, one can use it for detecting HB$_s$A$_g$ in a test sample, such as serum. This is done as follows:

For detecting hepatitis antigen (HB$_s$A$_g$) in serum, the reagent and test serum as to which the possible presence of HB$_s$A$_g$ is desired to be tested, are brought together and if there is HB$_s$A$_g$ in the serum, HB$_s$A$_g$ from the serum will react with free antibody reacting groups on the reagent to attach itself to the outermost coat of the reagent consisting of antibody to hepatitis surface antigen.

After washing, radioactively labeled antibody will be added to react with any such attached HB$_s$A$_g$ from the test serum. Any excess of radioactively labeled antibody beyond what has thus reacted is then removed and the presence or absence of significant radioactivity in what remains will determine the presence or absence of HB$_s$A$_g$ in the test serum, within the limits of sensitivity of the particular test.

This present process has been found to have very good sensitivity, as tests results tabulated hereinbelow with show.

Thus, the present invention involves a sensitive solid state process in which the presence of HB$_s$A$_g$ in the test serum can be determined without ever at any stage requiring the making of separate "dissociated" antibody in some separate process of manufacture, which latter is a very expensive part of all the previous processes, if good sensitivity is to be achieved. For this reason, this present process can be expected to be especially economical and inexpensive in its totality, as compared to any previous solid state process which might secure comparable sensitivity.

DETAILED DESCRIPTION

Figure 1:
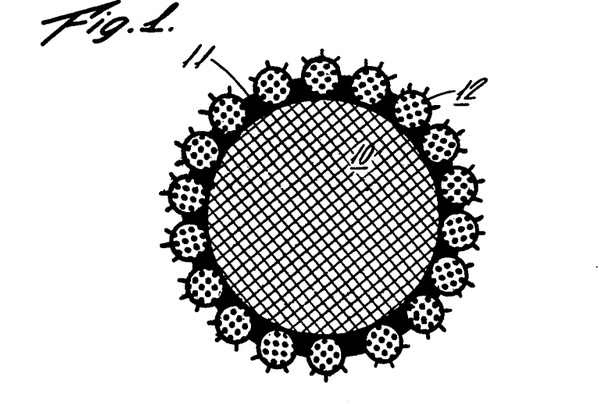
FIG. 1 is an enlarged diagrammatic representation of a cross section of a suitable bead with attached purified HB$_s$A$_g$ after the first stage of the process of the present invention, followed by washing, and also including a non-specific protein to cover any spaces not covered by the HB$_s$A$_g$.

Describing in illustration and not in limitation and including a preferred embodiment:

In FIG. 1, as already indicated, there is a substrate or purified part thereof, of a type which would be suitable for use in the solid state process, as discussed in Coller et al U.S. Pat. No. 3,872,225, for example in column 15 last paragraph on through column 16, first paragraph, which Coller et al U.S. Pat. No. 3,872,225 is hereby incorporated herein by reference in its entirety. More specifically, what is shown in FIG. 1 as a preferred illustration of what can be used as a substrate is a spherical polystyrene bead 10, which can preferably be approximately one-quarter inch in diameter.

On that bead, at the stage shown in FIG. 1, purified HB$_s$A$_g$ 12 has been applied as a coating on the outside surface of the bead but to an extent only which would permit coverage of it by its antibody, and any unattached residue of the HB$_s$A$_g$ has been washed off.

A non-specific protein 11, such as normal human serum, that is, such serum not containing HB$_s$A$_g$ or anti-HB$_s$, or human serum albumin (1% solution, for example, or more),—only 2 examples of such proteins, of which there are other examples,—is thereafter applied to cover any spaces on the surface of the bead which may happen not to have been covered by the HB$_s$A$_g$.

Figure 2:
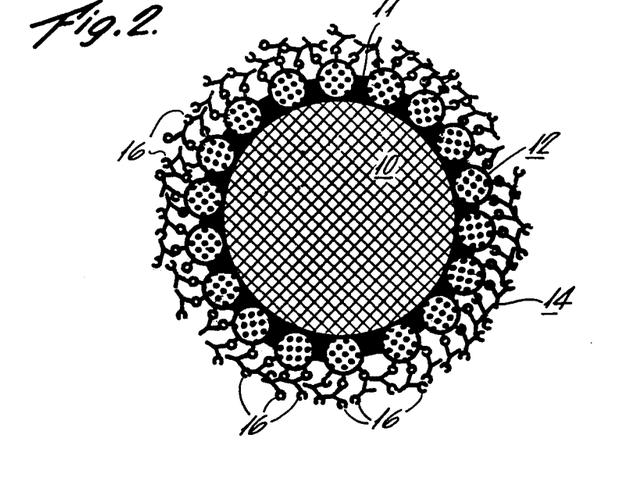
FIG. 2 is a similar representation, but including the further attachment of anti-HB$_s$ after the stage in which a source of such antibody is brought into contact sufficient to completely cover the HB$_s$A$_g$, with excess antibody reacting groups remaining free, followed by washing, and thus shows diagrammatically a particular bead ready to be used for testing.

In FIG. 2, anti-HB$_s$ 14 has been applied to an extent which completely covers the HB$_s$A$_g$, in the sense that all of the reacting sites of the HB$_s$A$_g$ are completely occupied by anti-HB$_s$, and leaves an excess 16 of antibody reacting sites free, followed by washing. This is the test reagent.

Figure 3:
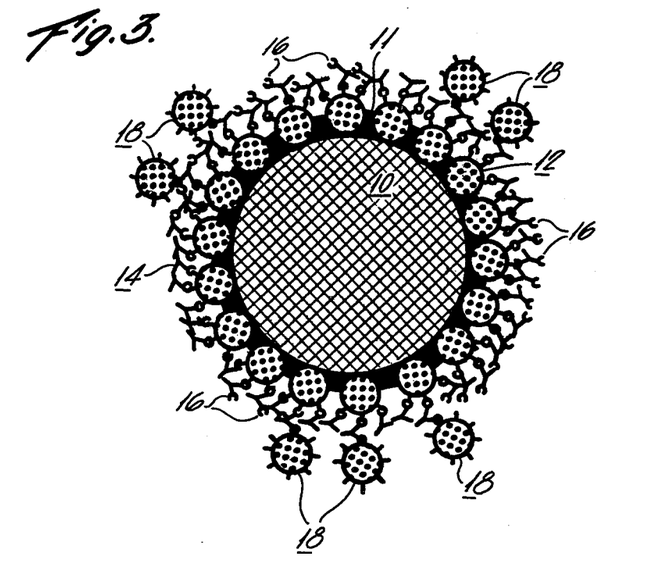
FIG. 3 is a similar representation, but after the particular test bead in question has been exposed to a sample to be tested for HB$_s$A$_g$, which sample happens to include HB$_s$A$_g$ which has attached itself to the anti-HB$_s$ which forms the outer coat of the test bead, followed by removal of the remainder of the test sample.

In FIG. 3, a test sample which is to be tested for the presence or absence of HB$_s$A$_g$, is brought into contact with the reagent. In this case the sample happens to be a test serum in which HB$_s$A$_g$ 18 was present and has attached itself to antibody, likewise followed by washing.

Figure 4:
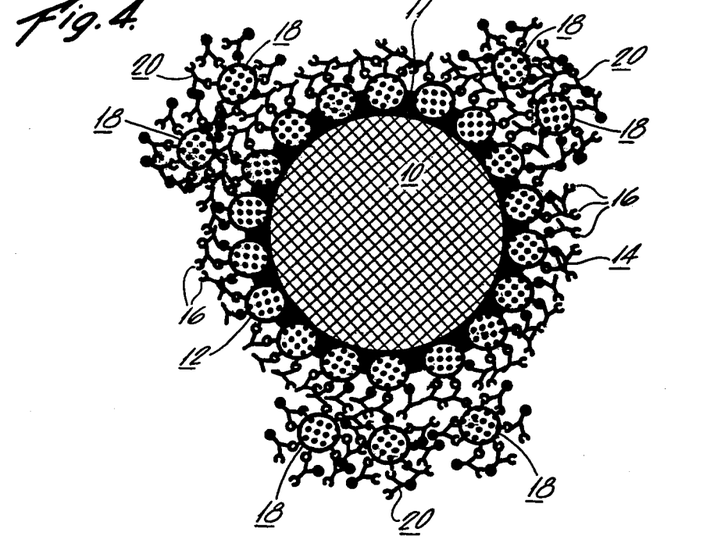
FIG. 4 is a similar representation, but at a stage where the bead of FIG. 3 has been contacted with radioactively labeled anti-HB$_s$, some of which antibody has attached itself to the HB$_s$A$_g$ from the test sample, followed by removal of the unattached radioactively labeled antibody, and thus enabling determination of the presence or absence of HB$_s$A$_g$ in the test sample, within the limits of sensitivity of the test, by the presence or absence of significant radioactivity in the test bead.

In FIG. 4, radioactive labeled anti-HB$_s$ 20 has been brought into contact with and attached itself to the HB$_s$A$_g$ from the test serum, and the whole has again been washed, preparatory to testing for significant radiation, which will of course in this case be present.

Recurring to the process to give a more specific explanation of a preferred embodiment, as indicated, the HB$_s$A$_g$ which forms the first coat should be a purified HB$_s$A$_g$.

The extent of purification required depends on whether the second coat, anti-HB$_s$, will be of animal or human origin. While the preference is for using the most purified fraction of HB$_s$A$_g$ for the initial coat, it has been found that HB$_s$A$_g$ fractions containing trace amounts of normal human serum protein could be used,—the trace amounts not interfering,—provided that the source of anti-HB$_s$ was human. In addition HB$_s$A$_g$ obtained from a human hepatoma cell line in tissue culture may also be used for the first coat. 10 and 100 fold tissue culture concentrates have been successfully used. (To get this, there can be, for example, pressure dialysis on an "Amicon" with XM 300 filter or centrifugation at 40,000 rpm in a Beckman Ti 60 rotor for 4 hours.)

In connection with the application of serum containing anti-HB$_s$ to the bead coated with HB$_s$A$_g$ and washed, if the concentrations of antigen and antibody are carefully standardized in appropriate amounts, as illustrated further on, and can readily be secured, there will be an excess of antibody reacting groups remaining free. It must be kept in mind that antibody is divalent and when reacted with an appropriate coating of antigen in sufficient quantity of antibody, many valences of the antibody will be free to react with more antigen.

Care at this point must be taken to assure that all of the reacting sites of the antigen (first coat) are substantially completely occupied by antibody.

It should be recognized that the sensitivity of this reagent can be regulated to a very fine degree. In general, the reagent can be made more sensitive by adding a more concentrated $HB_sA_g$ as the first coat, so that it will bind more anti-$HB_s$, which comprises the second coat. The more of the second coat bound, the more sensitive the reagent becomes. However, this is limited by the requirement of covering the first coat with the second. One must not put so much of the antigen on the substrate so as to be incapable of being covered by the antibody coat. Therefore, the limit of sensitivity of our reagent will be determined by the quality and concentration of anti-$HB_s$ which will be available for covering the antigen coat.

This reagent may be reacted with a test sample which may or may not contain $HB_sA_g$. If $HB_sA_g$ is present it will react with the antibody present on the bead. This is then washed and radioactively labeled antibody ($^{125}I$ labeled IgG fraction of anti-$HB_s$ antiserum) is added to react with the antigen. A positive assay is one where the radioactivity in the test bead is double or greater than that obtained normal test serum (negative for $HB_sA_g$).

Furthermore, it has been found that the $^{125}I$ labeled anti-$HB_s$ need not be "dissociated" antibody provided that the species from which the IgG was fractionated is the same as that from which the antibody was obtained for the second coat used in preparing the reagent. such as where human material is used in both cases. This may be the 50% saturated ammonium sulfate portion of anti-$HB_s$ antibody or the purified IgG (immune gamma globulin) portion eluted from a column of DEAE cellulose (DE-52, Whatman) or DEAE Sephadex (Pharmacia). The more purified the $HB_sA_g$ used as the first coat is, the less purified need be the $^{125}I$ labeled anti-$HB_s$.

The assay of the present invention can be called a "solid phase affinity radioimmunoassay", since it utilizes attachment of the purified $HB_sA_g$ to a substrate in the first step of the process making up the reagent, and the affinity involved as between $HB_sA_g$ and anti-$HB_s$ in the second step in which the highly specific antibody is self-selected to cover the $HB_sA_g$. It is a very sensitive assay, far more sensitive than any current type of radioimmunoassay for this purpose where anything but "dissociated" anti-$HB_s$ is used to cover the substrate. Furthermore, the present reagent would seem likely to have a significantly greater sensitivity than current types.

The avoidance of use of any separate process for making "dissociated" antibody makes the reagent of the present invention much more economical than an assay which requires separately made "dissociated" antibody.

Any protein adhering substrate can be used. In the examples which follow, the reagent was prepared by adsorption of the antigen (first coat) on three different substrate materials. These are:
1. polystyrene beads, $\frac{1}{4}''$ diameter (U.S. Plastic Corp., Lima, Ohio)
2. polystyrene tubes, 10×75 mm, (Falcon)
3. disposable microtiter plates, flat bottom, (Cooke Engineering Co., Alexandria, Va.).

A dilution of purified $HB_sA_g$ is chosen to coat the plastic substrate. As an illustration, it has been found that a 1 to 20 dilution (0.01 M Tris—HCl buffer—pH 9.0) of an antigen concentrate positive according to a test having the sensitivity approved by the U.S. Food and Drug Administration when diluted to 1 to 100,000 with normal human serum as diluent served the purpose.

The plastic substrate is allowed to remains in contact with the diluted $HB_sA_g$ for 2 hours at room temperature and overnight at 2° to 5° C. Minor changes of incubation times and temperatures may serve equally well and will be evident to trained immunologists.

The antigen solution is removed and the coated plastic substrate is washed with several rinses of distilled water.

The plastic substrate is next placed in contact with normal serum or a 1% solution of albumin, of any species, provided that the species is the same as that for the source of antibody used for the second coat of the process reagent and the radioactively labeled antibody, and incubated at 2° to 5° C. for 18 hours.

The coated plastic substrate is next washed with distilled water. A test sample, e.g., serum containing high titered antibody (1/64000 by passive hemagglutination assay has served the purpose) is allowed to react with the washed beads for 2 hours at room temperature and overnight at 2° to 5° C. The beads are washed with several rinses of distilled water.

It is important, at this point, to use an antiserum of sufficiently high titer to occupy all of the antigen (first coat) reacting sites. If this is not possible one can either concentrate the antiserum or use a higher dilution (1/30, 1/40) of antigen ($HB_sA_g$) for the first layer. The correct proportions of antigen and antibody can readily be determined by adding radioactively labeled ($^{125}I$) antibody to the double layered beads. If all of the antigen reacting sites were covered with cold (not radioactive) antibody there should be no attachment of radioactive ($^{125}I$) labeled antibody. The washed double layered beads may be drained dry and stored in the cold (2° to 5° C.), being careful to refrigerate but not freeze, until ready for use as one of the assay reagents. When stored dry in the cold it would be expected that the beads should remain effective for assay of $HB_sA_g$ for years.

A second reagent is required to determine whether a test sample is positive. This reagent is radioactive $^{125}I$ labeled anti-$HB_s$ IgG. Another advantage of the present invention is that the aforesaid second reagent need not be "dissociated" antibody. Use has been made of 50% saturated ammonium sulfate precipitates of high titered anti-$HB_s$ as well as more purified DEAE cellulose fractionated anti-$HB_s$ immune globulin G.

The labeling technique that has been used for the second reagent is a modification of that of Greenwood, Hunter and Glover, Biochemical J. 89:114 (1963), which article is hereby incorporated by reference and see also Coller et al U.S. Pat. No. 3,872,225, already incorporated by reference in its entirety, as to which column 6 is especially pertinent.

Method of Labeling the Antibody

The specific modified method of labeling antibody which was actually used was as follows:

The following reagents were added, in order, to a small conical vessel: 20 ul of 0.25 M phosphate buffer, pH 7.4; 200 uC (micro-Curies) of high specific activity $^{125}I$ (in 1 to 2 ul); 10 ug of anti-$HB_s$ gamma globulin (in 10 ul); 15 ul of a solution of chloramine T (3.5 ug/ul). The vial is vortexed for 15 seconds after which is added 20 ul of a solution of sodium metabisulfite (4.8 ug/ul); 20 ul of a solution of sucrose (22.5%); potassium iodide (2 mg/ml) and aqueous phenol red (0.025%). The mixture was applied to the top of a 300×25 mm column packed with Sephadex G 200 and equilibrated with phosphate buffered saline, pH 7.4. The proteins eluted from the column were monitored and fractions comprising the first peak of radioactivity were pooled and diluted with an equal volume of fetal calf serum. This stock solution, stored at 2° to 5° C., was useful for approximately 4 weeks and was diluted 1:2 with fetal calf serum just prior to use.

In the case of actual production, the amounts can simply be increased without changing the proportions.

The essential in this respect is to use a resin in a column which would effectively separate unreacted labeled K iodide ($I^{125}$) from the protein. There are in fact various methods of labeling and purifying in connection with this process, as the previously mentioned Coller patent will make evident.

Exemplary Specifics of the Test Proper

To assay for $HB_sA_g$, in serum, for example, the test serum is added to the solid reagent of the present invention. If test tubes or microtiter plates are used for the present invention, then the volume of test serum must be less than the height of attached reagent (layers). If beads are used for the present invention's solid reagent, then the amount of test serum should be sufficient to cover the beads (¼" beads require 0.2 ml serum). Incubate either overnight at room temperature or for 2 hours at 45° C. Aspirate and wash with distilled water. Add the second reagent (labeled anti-$HB_s$) in the same volume as test serum. Incubate for 1 hour at 45° C. Aspirate and wash. Tubes and beads placed in tubes are then counted in a suitable gamma counter, as gone into more fully in the previously mentioned Coller patent. If microtiter plates are used, the wells are cut out and placed in tubes for counting. A mean of 7 known negative sera may be used to compare with test sera. A test serum count divided by the mean of negative sera count of 2 or more is considered positive.

In the present invention, the preferred forms of reagent and process are those using beads and preferably polystyrene and about ¼" in diameter.

As far as concentration of certain items is concerned, the preference is to use the most concentrated source of anti-$HB_s$ in unpurified non-dissociated form which can reasonably and practicably be secured, and the most concentrated form of purified $HB_sA_g$ which such anti-$HB_s$ can as a practical matter completely cover when the purified $HB_sA_g$ is on the substrate, leaving an excess of antibody reacting sites in a free state. As already indicated, this can readily be determined by testing the surface afterwards by means of labeled anti-$HB_s$ to see whether any of the $HB_sA_g$ on the undercoat has not already been covered by unlabeled anti-$HB_s$.

It has been found that with ordinary sources of anti-$HB_s$ such as now in normal use, and use of original purified $HB_sA_g$—carrying serum of a strength which when diluted to 1 to 100,000 with normal human sera will show positive on a test of the sensitivity now approved by the U.S. Food and Drug Administration, when used with beads the original purified—$HB_sA_g$—carrying serum can and preferably should be used in our reagent and process in a dilution of 1 to 20, and in the ordinary case where no unusually highly concentrated source of impure and undissociated anti-$HB_s$ is available, use of such a dilution in the case of the beads is preferred and use of the beads along with such dilution is the preference.

Where test tubes or micro-titer plates are used, these less preferred forms should likewise preferably be the same ordinary source of impure, undissociated anti-$HB_s$ and the same original purified $HB_sA_g$—carrying serum; a dilution of that serum of 1 to 10 can and should preferably be used, although the ultimate greatest preference is still the polystyrene beads with the 1 to 20 dilution of the purified—$HB_sA_g$—carrying serum in case of use of ordinary impure and unpurified anti-$HB_s$ sources.

Tables 1-4 show the performance of assays using the present invention's reagent. Note from table 4 that one can dilute the test serum 10,000 times and still detect a positive reaction by virtue of having a ratio of 2 or more. Table 1 used a concentrate of $HB_sA_g$ from a human carrier donor purified and concentrated as mentioned. Table 4 shows activity of the reagent in question when using dilutions of hepatitis B serum of subtype adw of 1-10 to 1-100,000. The test is sensitive to 1 to 10,000.

In table 4, the first coat applied to the beads of the present reagent was a concentrate of human primary liver carcinoma (hepatoma) tissue culture fluid harvested after 7 days. The tissue culture fluid was concentrated by "Amicon" pressure dialysis on an XM 300 filter 100 fold. The concentrate used was one which could be detected by a test of the sensitivity called for by the U.S. Food and Drug Administration when that concentrate was in a 1 to $10^6$ dilution.

Beads were coated with a 1-10 and 1-20 dilution of this concentrate.

For the second coat either a combination of human and goat anti-$HB_s$ (an equal mixture of the IgG fraction of both concentrated 10 fold) or the human anti-$HB_s$ IgG fraction alone concentrated 10 fold was used. The results show that when the present invention's beads were given a first coating of $HB_sA_g$ in a dilution of 1-20 and then coated with anti-$HB_s$ of either the mixture of human and goat immune globulins or human immunoglobulin alone the sensitivity was good up to and including a dilution of 1 to 10,000. When the initial coating of this invention was 1-10 of the $HB_sA_g$ concentrate the sensitivity was slightly less. The limit at which sufficient sensitivity was secured was approximately 1 to 10,000.

Tests for a particular serum of the ayw. subtype were also made and produced substantially similar results.

It is possible, if desired, in making the reagent of the present invention, to use purified $HB_sA_g$ from a nonhuman primate which is a carrier, instead of using a human source.

In the tables, in all cases, the results are expressed in a ratio of the test cpm (counts per minute) to the cpm of a mean of 7 negatives.

The mean of the 7 negatives in table 1 was 319, in table 2 was 142, in table 3 was 172, in table 4 by columns, column 1 was 347±35.72, column 2 was 310±23.52, column 3 was 307±29.43, and column 4 was 292±25.85.

In all cases in the tables, washing was duly performed after each step in what was done in the process from the beginning up to the actual reading of the values.

In table 1 and table 2 which involved the present invention with test tubes, 7.5×1.2 cm polystyrene tubes were used for the reagent of the present invention. The first coat was 200 ul HB$_s$A$_g$ (1-10 dilution) in 0.01 M Tris pH 9.0. The source of non-specific protein was 400 ul normal human serum and the second coat was 400 ul human globulin anti-HB$_s$ (IgG).

In table 3, which involved disposable microtiter plates, (U type), the plates were incubated with 100 microliters HB$_s$A$_g$ (1-10) in Tris at pH 9.0 for 18 hours at room temperature. It was then washed. 200 ul of normal human serum was added. Then after washing, 200 ul of human anti-HB$_s$ (IgG) was added and it was washed.

In table 4, which involved beads, insofar as a product of the goat was used it was not IgG, but where human was used it was IgG.

Polystyrene beads of ¼" diameter from the U.S. Plastic Corporation of 1550 Elida Road, Lima, Ohio 45805 were used.

In table 4, involving the use of the present reagent with polystyrene beads, the first two sets of values involved use of a 1 to 10 dilution of HB$_s$A$_g$ in the first coating, with the second coating in the first set of values having as the source of anti-HB$_s$, goat and human in a 1 to 1 ratio to each other and in the second set of values, all human.

The last two sets of values involved use of a 1 to 20 dilution of HB$_s$A$_g$ in the first coating with again the first of them involving in the second coating, 1-1 goat and human source and the second set of values again involving all human in the second coating.

The values in table 4 are all shown against a series of different dilutions of HB$_s$A$_g$ in normal human serum, after starting with serum from the one particular single patient with chronic hepatitis B.

In tables 1, 2 and 3, it will be noted that the ratios are given for two individually run reagents for each test serum.

In view of our invention and disclosure, variations and modifications to meet individual whim or particular need will doubtless become evident to others skilled in the art, to obtain all or part of the benefits of our invention without copying the process and composition shown, and we, therefore, claim all such insofar as they fall within the reasonable spirit and scope of our claim.

Table I

Assay of Different Sera Using the Present Reagent With Polystyrene Tubes

Ratio $\frac{\text{cpm test}}{\text{cpm mean NHS* (7)}}$

| Sample | Ratio |
|---|---|
| 256547 | 18.3, 19.6 |
| 25656 | 12.0, 10.8 |
| 25646 | 11.9, 11.7 |
| 25692 | 24.2, 24.0 |
| 209001 | 21.8, 17.4 |
| 248240 | 19.4, 20.0 |
| 209003 | 2.3, 2.3 |
| 232349 | 2.23, 2.4 |
| 248244 | 18.5, 21.6 |
| 209008 | 19.6, 19.4 |
| 248197 | 21.9, 19.6 |
| 248199 | 15.2, 15.1 |
| 243413 | 1.3, 1.8 |
| 243415 | 1.9, 1.4 |
| 243418 | 0.99, 1.4 |

*NHS = Normal human serum

Table 2

A Second Assay of Different Sera Using the Present Reagent with Polystyrene Tubes Ratio $\frac{\text{cpm test}}{\text{cpm mean NHS (7)}}$

| Sample | Ratio |
|---|---|
| 261249 | 23.9, 18.9 |
| 261277 | 1.2, 7.9 |
| 209001 | 21.4, 19.1 |
| 248252 | 18.4, 18.8 |
| 248245 | 21.2, 20.6 |
| 248233 | 26.5, 24.2 |
| 25645 | 16.5, 16.2 |
| 25464 | 15.0, 13.4 |
| 25651 | 12.2, 10.8 |
| 243552 | 0.84, 0.99 |
| 261922 | 1.2, 1.2 |
| 261923 | 1.02, 1.8 |
| 261924 | 0.98, 0.68 |
| 261927 | 0.86, 0.62 |

Table 3

Assay of Different Sera Using the Present Reagent with Disposable Microtiter Plates Ratio $\frac{\text{cpm test}}{\text{cpm mean NHS (7)}}$

| Sample | Ratio |
|---|---|
| 25783 | 5.05, 5.1 |
| 25766 | 1.45, 7.41 |
| 25714 | 10.1, 8.3 |
| 25692 | 16.1, 18.4 |
| 25687 | 11.2, 9.8 |
| 25678 | 9.0, 7.2 |
| 25676 | 10.8, 12.1 |
| 25653 | 7.0, 4.4 |

Table 4

Assay Using the Present Reagent with Polystyrene Beads, but Varying the Dilutions of HB$_s$A$_g$ and the Particular Source of Anti-HB$_s$ Ratio $\frac{\text{cpm test}}{\text{cpm mean of NHS (7)}}$

| Dilution of HB$_s$A$_g$ "adw" in normal human sera in subject matter under test | Polystyrene beads First coating 1-10 Dilution HB$_s$A$_g$ | | Polystyrene beads First Coating 1-20 Dilution HB$_s$A$_g$ | |
|---|---|---|---|---|
| | 1 2d coating Source: goat & human 1-1 | 2 2d coating Source: human | 3 2d coating Source: goat & human 1-1 | 4 2d coating Source: human |
| 1-10 | 23.6 | 25.1 | 17.7 | 25.8 |

Table 4-continued

Assay Using the Present Reagent with Polystyrene Beads, but Varying the Dilutions of $HB_sA_g$ and the Particular Source of Anti-$HB_s$ Ratio $\frac{\text{cpm test}}{\text{cpm mean of NHS (7)}}$

| Dilution of $HB_sA_g$ "adw" in normal human sera in subject matter under test | Polystyrene beads First coating 1-10 Dilution $HB_sA_g$ | | Polystyrene beads First Coating 1-20 Dilution $HB_sA_g$ | |
|---|---|---|---|---|
| | 1 2d coating Source: goat & human 1-1 | 2 2d coating Source: human | 3 2d coating Source: goat & human 1-1 | 4 2d coating Source: human |
| 1-100 | 13.6 | 22.1 | 18.8 | 20.8 |
| 1-1000 | 9.4 | 14.3 | 9.6 | 15.5 |
| 1-2000 | 7.6 | 8.9 | 7.1 | 16.3 |
| 1-3000 | 6.8 | 8.3 | 6.2 | 11.8 |
| 1-4000 | 5.0 | 4.5 | 5.1 | 8.9 |
| 1-5000 | 3.7 | 3.9 | 4.3 | 9.3 |
| 1-6000 | 3.9 | 3.7 | 3.5 | 7.3 |
| 1-7000 | 3.0 | 4.3 | 3.3 | 5.5 |
| 1-8000 | 3.0 | 2.6 | 2.7 | 5.2 |
| 1-10,000 | 2.5 | 2.0 | 2.6 | 3.9 |
| 1-100,000 | 1.1 | 1.2 | 0.95 | 1.2 |

Having thus described our invention, what I claim as new and desire to secure by Letters Patent is:

1. A reagent for use in determining the presence of $HB_sA_g$, in a test sample said reagent comprising a substrate having thereon a first coat comprising $HB_sA_g$, and a second coat comprising anti-$HB_s$ which substantially completely covers said first coat of $HB_sA_g$, said anti-$HB_s$ substantially completely occupying the reacting sites of the $HB_sA_g$ and leaving a substantial excess of antibody reacting sites remaining free, whereby the anti-HB stands ready to react with any $HB_sA_g$ present in a test sample to which said reagent is added.

2. A reagent according to claim 1 in which the substrate is a test tube.

3. A reagent according to claim 2 in which the test tube is plastic.

4. A reagent according to claim 2 in which the test tube is glass.

5. A reagent according to claim 3 in which the plastic is selected from the group consisting of polystyrene, polypropylene and polycarbonate.

6. A reagent according to claim 1 in which the substrate is a plastic microtiter plate.

7. A reagent according to claim 1 in which the substrate is a bead.

8. A reagent according to claim 7 in which the bead is plastic.

9. A reagent according to claim 7 in which the bead is glass.

10. A reagent according to claim 8 in which the plastic is selected from the group consisting of polystyrene, polypropylene, and polycarbonate.

11. A reagent according to claim 1 in which the first coat additionally comprises a non-specific protein, fills in the spaces on the substrate not coated by $HB_sA_g$.

12. A method for determining the presence of $HB_sA_g$ in a test sample which comprises the steps of (a) forming a reagent by coating a substrate with a first coat comprising $HB_sA_g$ washing the $HB_sA_g$-coated substrate, thereafter substantially completely covering the $HB_sA_g$ with a second coat comprising anti-$HB_s$, said anti-$HB_s$ substantially completely occupying the reacting sites of the $HB_sA_g$ and leaving a substantial excess of antibody reacting sites remaining free, and washing the reagent thus formed, (b) thereafter exposing said reagent to a test sample which is to be tested for the presence of $HB_sA_g$ thereby allowing $HB_sA_s$ which may be present in the test sample to attach itself to the anti-$HB_s$ on the reagent, (c) washing the reagent, (d) thereafter contacting the reagent thus exposed with radioactively labeled anti-$HB_s$, (e) washing the reagent, and (f) thereafter testing the reagent thus contacted for radioactivity.

13. A method according to claim 12 in which the source of the $HB_sA_g$ used for originally coating the substrate is a human primary liver carcinoma cell line in tissue culture.

14. A method according to claim 12 in which the source of the $HB_sA_g$ used for originally coating the substrate is a human carrier of $HB_sA_g$.

15. A method according to claim 12 in which after the substrate is originally coated with $HB_sA_g$ and washed, contact is had between the substrate and a non-specific protein, which fills in the spaces on the substrate not coated by $HB_sA_g$.

16. A method of making a reagent for use in determining the presence of $HB_sA_g$ in a test sample which comprises the steps of (a) coating a substrate with a first coat comprising $HB_sA_g$, (b) washing the $HB_sA_g$-coated substrate, (c) thereafter substantially completely covering the $HB_sA_g$ with a second coat comprising anti-$HB_s$, said anti-$HB_s$ substantially completely occupying the reacting sites of the $HB_sA_g$ and leaving a substantial excess of antibody reacting sites remaining free, and (d) washing the reagent thus formed.

17. A method according to claim 16 in which the source of the $HB_sA_g$ used for originally coating the substrate is a human primary liver carcinoma cell line in tissue culture.

18. A method according to claim 16 in which the source of the $HB_sA_g$ used for originally coating the substrate is a human carrier of $HB_sA_g$.

19. A method according to claim 16 in which after the substrate is originally coated with $HB_sA_g$ and washed, contact is had between the substrate and a non-specific protein, which fills in the spaces on the substrate not coated by $HB_sA_g$.

20. A method according to claim 16 in which the source of the $HB_sA_g$ used for originally coating the substrate is a non-human primate carrier of $HB_sA_g$.

21. A reagent according to claim 1 in which the substrate is a plastic.

22. A reagent according to claim 1 in which the substrate is glass.

23. A reagent according to claim 21 in which the plastic is selected from the group consisting of polystyrene, polypropylene and polycarbonate.

* * * * *

UNITED STATES PATENT AND TRADEMARK OFFICE
CERTIFICATE OF CORRECTION

PATENT NO. : 4,189,464

DATED : February 19, 1980

INVENTOR(S) : Baruch S. Blumberg and Irving Millman

It is certified that error appears in the above—identified patent and that said Letters Patent are hereby corrected as shown below:

In the Abstract:

line 1, delete "reagent" (second occurrence);
line 4, after "washing" insert --the--;
line 7, delete "as a second coat" (second occurrence);
line 17 and 18, delete "is brought into contact with the reagent" (second occurrence);
line 20 and 21, delete "sample is determined" (second occurrence).

In the Specification:

Col. 3, line 25, "with" should be --will--;

Col. 5, line 30, after "obtained" insert --using--;

Col. 6, line 9, "remains" should be --remain--;
line 24, delete "A test sample, e.g.,";
line 24, "serum" should be --Serum--.

UNITED STATES PATENT AND TRADEMARK OFFICE
CERTIFICATE OF CORRECTION

PATENT NO. : 4,189,464
DATED : February 19, 1980
INVENTOR(S) : Baruch S. Blumberg and Irving Millman It is certified that error appears in the above-identified patent and that said Letters Patent are hereby corrected as shown below:

In the Claims:

Claim 11, line 2, after "protein," insert --which--.

Claim 19, line 4, "spaces" should be --space--.

Signed and Sealed this

Eighth Day of July 1980

[SEAL]

Attest:

Attesting Officer

SIDNEY A. DIAMOND

Commissioner of Patents and Trademarks

UNITED STATES PATENT AND TRADEMARK OFFICE
CERTIFICATE OF CORRECTION

PATENT NO. : 4189464
DATED : February 9, 1980
INVENTOR(S) : Baruch S. Blumberg and Irving Millman It is certified that error appears in the above-identified patent and that said Letters Patent are hereby corrected as shown below:

Claim 1, line 9, "anti-HB" should be --anti-HBs--.

Signed and Sealed this

Tenth Day of November 1981

[SEAL]

Attest:

GERALD J. MOSSINGHOFF

Attesting Officer     Commissioner of Patents and Trademarks